United States Patent [19]
Houlihan

[11] Patent Number: 5,284,836
[45] Date of Patent: Feb. 8, 1994

[54] HETEROCYCLIC PHOSPHOLIPIDS USEFUL IN TREATING MULTIPLE SCLEROSIS

[75] Inventor: William J. Houlihan, Mountain Lakes, N.J.

[73] Assignee: Sandoz Ltd., Basel, Switzerland

[21] Appl. No.: 985,994

[22] Filed: Dec. 4, 1992

Related U.S. Application Data

[60] Division of Ser. No. 752,739, Aug. 30, 1991, Pat. No. 5,182,271, which is a division of Ser. No. 533,246, Jun. 5, 1990, Pat. No. 5,064,816, which is a continuation-in-part of Ser. No. 489,578, Mar. 7, 1990, abandoned, which is a continuation-in-part of Ser. No. 423,323, Oct. 18, 1989, abandoned, which is a continuation-in-part of Ser. No. 392,187, Aug. 10, 1989, abandoned.

[51] Int. Cl.$^5$ ............... A61K 31/685; A61K 31/67
[52] U.S. Cl. ...................... 514/77; 514/95; 514/99; 514/903; 549/8; 549/218
[58] Field of Search ............ 514/79, 77, 89, 95, 514/903

[56] References Cited
U.S. PATENT DOCUMENTS

| | | | |
|---|---|---|---|
| 4,673,672 | 6/1987 | Houlihan et al. | 514/95 |
| 4,749,696 | 6/1988 | Lee | 514/89 |
| 4,778,788 | 10/1988 | Munder | 514/77 |
| 5,049,552 | 9/1991 | Eibl | 514/77 |

OTHER PUBLICATIONS

E. Bosies et al., *Lipids*, vol. 22, pp. 947–951 (1987).
I. Kudo, et al. *Lipids*, vol. 22, pp. 862–867 (1987).

*Primary Examiner*—Frederick E. Waddell
*Assistant Examiner*—T. J. Criares
*Attorney, Agent, or Firm*—Robert S. Honor; Melvyn M. Kassenoff; Joseph J. Borovian

[57] ABSTRACT

The invention discloses certain heterocyclic, thioether, keto-ester and alkyl phospholipids, e.g., heterocyclic phospholipids having the formula

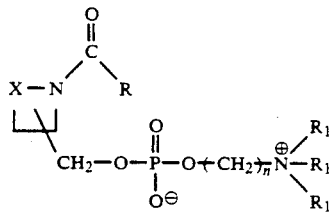

where R is n-$C_{14}$–$C_{20}$alkyl or O-n-$C_{14}$–$C_{20}$alkyl; each $R_1$ is methyl or ethyl; n is 2–6; and X is $+CH_2+_m$, where m is 2–4, $CH_2CH_2O$ or $CH_2CH_2S$, or a corresponding hydrate thereof, which compounds are useful in treating multiple sclerosis.

10 Claims, No Drawings

HETEROCYCLIC PHOSPHOLIPIDS USEFUL IN TREATING MULTIPLE SCLEROSIS

This is a division of application Ser. No. 07/752,739, filed Aug. 30, 1991 now issued as U.S. Pat. No. 5,182,271 which in turn is a division of application Ser. No. 07/533,246, filed Jun. 5, 1990, now issued as U.S. Pat. No. 5,064,816, which in turn is a continuation-in-part of U.S. Pat. application Ser. No. 07/489,578, filed Mar. 7, 1990, now abandoned which in turn is a continuation-in-part of U.S. Pat. application Ser. No. 07/423,323, filed Oct. 18, 1989, now abandoned which in turn is a continuation-in-part of U.S. Pat. application Ser. No. 07/392,187, filed Aug. 10, 1989, now abandoned.

The present invention relates to the use of certain heterocyclic, thioether, keto-ester and alkyl phospholipids useful in treating multiple sclerosis.

Multiple sclerosis, a crippling nerve disorder characterized by disseminated patches of demyelination in the brain and spinal cord, has occupied the attention of research organizations for many years without, unfortunately, any appreciable success. Although ACTH (adrenocorticotropic hormone) or prednisone appears to hasten recovery in acute attacks, especially when administered early in the episode, there is no specific therapy, even today, as spontaneous remissions make any treatment difficult to evaluate.

U.S. Pat. No. 4,778,788 discloses certain lysolecithin analogs useful in treating multiple sclerosis.

It has now been found that, surprisingly, certain heterocyclic, thioether, keto-ester and alkyl phospholipids are useful in treating multiple sclerosis. One class of compounds found useful in the practice of this invention is the heterocyclic phospholipids of formula I:

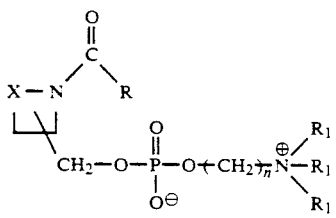

where
R is n-$C_{14}$-$C_{20}$alkyl or O-n-$C_{14}$-$C_{20}$alkyl;
each $R_1$, independently, is methyl or ethyl;
n is an integer 2 to 6; and
X is $-(CH_2)_m-$, where m is 2 to 4; $CH_2CH_2O$ or $CH_2CH_2S$;
and the corresponding hydrates thereof.

Included among the compounds of formula I are the compounds of subclass Ia:

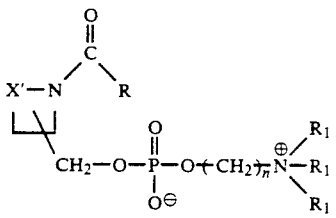

where
X' is $-(CH_2)_{2-4}-$, and R,
each $R_1$ and n are as defined above;
and the corresponding hydrates thereof.

The preferred compounds of subclass Ia are the compounds of formula Ia':

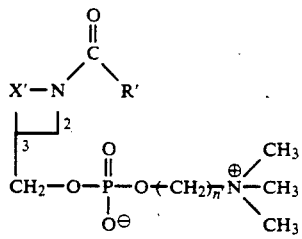

where
R' is n-$C_{14}$-$C_{18}$alkyl or O-n-$C_{14}$-$C_{18}$alkyl;
n' is an integer 2 to 4; and
X' is as defined above;
and the corresponding hydrates thereof.

The most preferred compounds of subclass Ia are 2-[[hydroxy[(1-octadecyloxycarbonyl-3-piperidinyl) -methoxy]phosphinyl]oxy]-N,N,N-trimethylethanaminium hydroxide inner salt-4-oxide having the formula

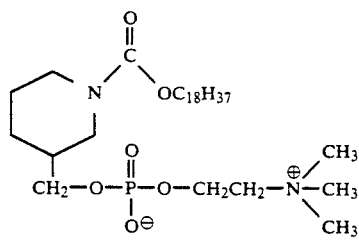

(hereinafter referred to as SDZ 62-826);
(±)-2-[[hydroxy[(1-octadecyloxycarbonyl-3-pyrrolidinyl) -methoxy]phosphinyl]oxy]-N,N,N-trimethylethanaminium hydroxide inner sale-4-oxide, dihydrate having the formula

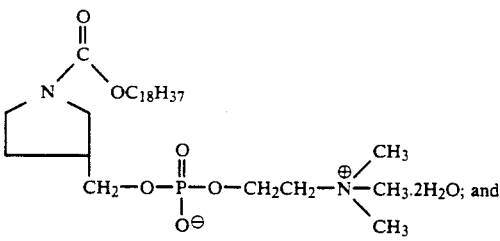

(±)-2-[[hexahydro-1-octadecyloxycarbonyl-1H-azepin-3-yl) -methoxy]hydroxy phosphinyl]oxy]-N,N,N-trimethylethanaminium hydroxide inner salt-4-oxide, 1.5 hydrate having the formula

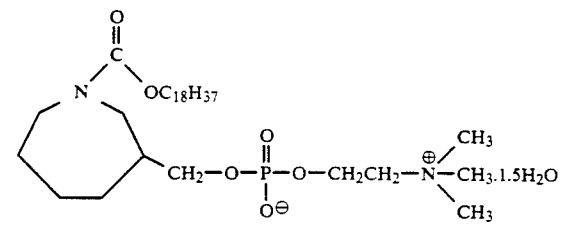

The compounds of subclass Ia where X' is $-(CH_2)_3-$ and R, each $R_1$ and n are as defined above and their use as anti-tumor agents are disclosed in U.S. Pat. No. 4,749,696. In any event, all of the compounds of subclass Ia may be prepared according to the processes set forth in said U.S. patent.

Also included among the compounds of formula I are the compounds of subclass Ib:

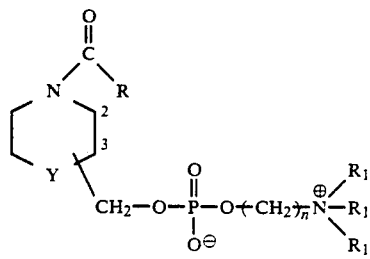

where

Y is —O— or —S—, and R, each $R_1$ and n are as defined above;

and the corresponding hydrates thereof.

The preferred compounds of subclass Ib are the compounds of formula Ib':

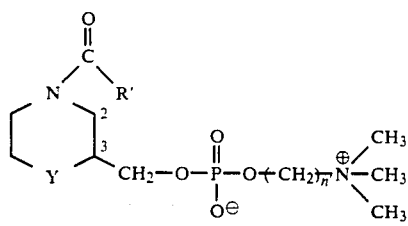

where Y, $R^1$ and n' are as defined above; and the corresponding hydrates thereof.

The most preferred compounds of subclass Ib are (±)-2-[[hydroxy[(4-octadecyloxycarbonyl-2-morpholinyl)-methoxy]phosphinyl]oxy]-N,N,N-trimethylethanaminium hydroxide inner salt-4-oxide, trihydrate having the formula

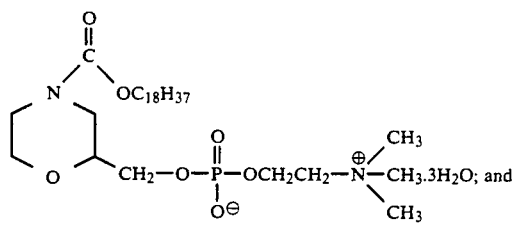

(±)-2-[[hydroxy[(tetrahydro-4-octadecyloxycarbonyl-2H-1,4-thiazin-2-yl)methoxy]phosphinyl]oxy]-N,N,N-trimethylethanaminium hydroxide inner salt-4-oxide, monohydrate having the formula

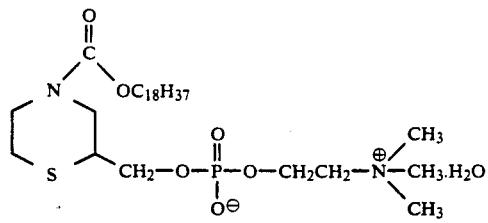

All of the compounds of subclass Ib may be prepared according to the processes set forth in U.S. Pat. No. 4,749,696.

Another class of compounds found useful in the practice of this invention is the thioether phospholipids of formula II:

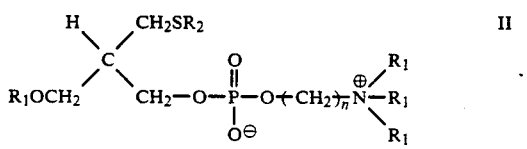

where $R_2$ is n-$C_{14}$-$C_{20}$alkyl, and each $R_1$ and n are as defined above.

The preferred compounds of formula II are compounds of formula II':

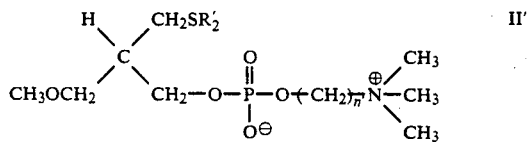

where $R_2'$ is n-$C_{14}$-$C_{18}$alkyl, and n' is as defined above.

The most preferred compound of formula II is 3-hexadecylmercapto-2-methoxymethylpropyl-2'-trimethylammonio-ethyl phosphate having the formula

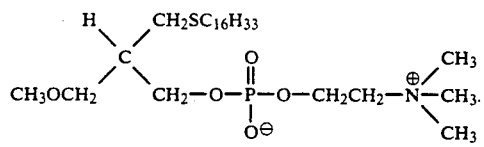

The compounds of formula II and their use as antitumor agents are disclosed in E. Bosies, et al, Lipids, Vol. 22, pgs. 947–951 (1987). In any event, all of the compounds of formula II may be prepared according to the processes described in the E. Bosies, et al article.

A further class of compounds found useful in the practice of this invention is the heterocyclic phospholipids of formula III:

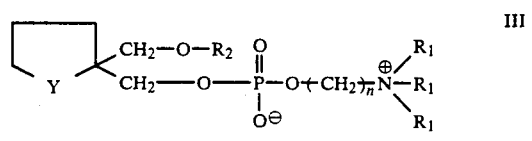

where Y, $R_2$, n and each $R_1$ are as defined above.

The preferred compounds of formula III are compounds of formula III':

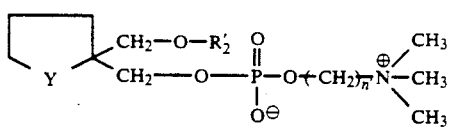

III' where Y, $R_2'$ and n' are as defined above.

The most preferred compound of formula III is 2-[[2-octadecyloxymethyltetrahydro-2-furanylmethoxy)-hydroxyphosphinyloxy]-N,N,N-trimethylethanaminium hydroxide inner salt-4-oxide having the formula

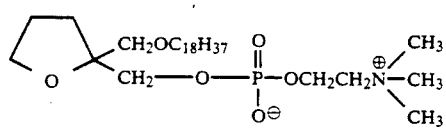

(hereinafter referred to as SDZ 62-834).

The compounds of formula III and their use as antitumor agents are disclosed in U.S. Pat. No. 4,673,672. In any event, all of the compounds of formula III may be prepared according to the processes described in said U.S. patent.

Still another class of compounds found useful in the practice of this invention is the keto-ester phospholipids of formula IV:

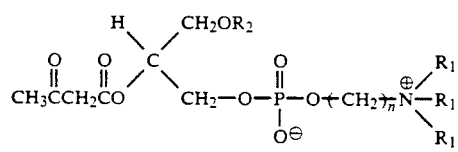

IV where $R_2$, each $R_1$ and n are as defined above.

The preferred compounds of formula IV are compounds of formula IV':

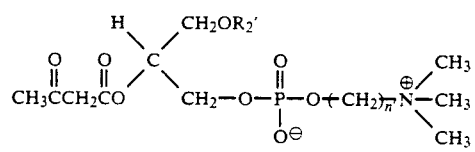

IV' where $R_2'$ and n' are as defined above.

The most preferred compound of formula IV is 3,5,9-trioxa-4-phosphaheptacosan-1-aminium, 7-(1,3-dioxobutoxy)-N,N,N-trimethyl, hydroxide inner salt, 4-oxide having the formula

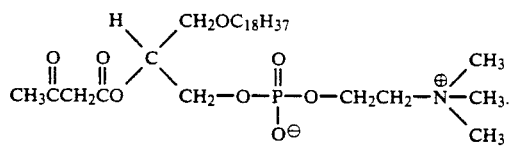

The compounds of formula IV and their use as antitumor agents are disclosed in I. Kudo, et al, Lipids, Vol. 22, pgs. 862-867 (1987). In any event, all of the compounds of formula IV may be prepared according to the processes described in the I. Kudo, et al article.

Yet still another class of compounds found useful in the practice of this invention is the alkyl phospholipids of formula V:

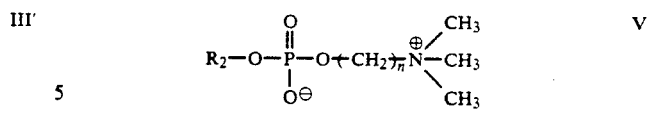

V where $R_2$ and n are as defined above.

The preferred compounds of formula V are compounds of formula V':

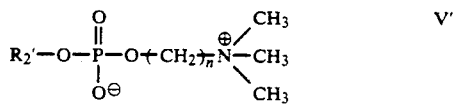

V' where $R_2'$ and n are as defined above.

The most preferred compound of formula V is the compound hexadecyl-2-trimethylammonioethylphosphate having the formula:

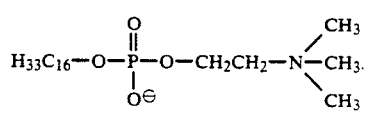

The compounds of formula V and their use as antitumor agents are disclosed in European Patent 225,608. In any event, all of the compounds of formula V may be prepared in accordance with the processes set forth in said European patent.

As is evident to those skilled in the art, the compounds of formulae I, II, III and IV contain an asymmetric carbon atom. It should be understood, therefore, that the compounds may exist in racemic or enantiomeric form and all forms are included within the practice of this invention. Enantiomeric forms may be recovered in conventional manner, e.g., by resolution of end or intermediate products or by employing optically active starting materials.

As indicated above, all of the compounds of formulae I, and the corresponding hydrates, II, III, IV and V are useful in treating multiple sclerosis. This property can be demonstrated employing the general methodology described by Borel et al in Agents and Action, 6, 468 (1976).

Experimental Allergic Encephalomyelitis (EAE) is induced in groups of 8 to 12 Wistar (♀) or Lewis (♀) rats each weighing 150 to 200 g by intradermal injection into each hind foot pad of 0.1 ml of an emulsion comprising 2.5 g bovine spinal cord (lyophylized and reconstituted with 12 ml $H_2O$), 1.5 ml Arlacel A, 8.0 ml Nujol and 0.2 ml saline containing 20 mg killed, dried Mycrobacterium phlei. The test compounds is administered at dosages of from 5 to 50 mg/kg/day p.o. 5 days a week, commencing on the day of sensitization and continuing for 3 weeks. Onset of EAE in control groups receiving no medication generally commences between 9 to 16 days after sensitization and is marked by symptoms of paralysis in the hind limbs and tail. Test animals are examined daily for symptoms of the disease and disease occurrence is scored as positive when complete involvement of both hind legs and tail is observed. The test animals are kept under observation for a total period of 25 days.

On administration of SDZ 62-826 and SDZ 62-834 at the above indicated dosage rates, a substantial reduction of occurrence of EAE is observed over the test period in comparison with occurrence in control groups receiving placebo.

The usefulness of the compounds of formulae I, II, III, IV and V in treating multiple sclerosis may also be demonstrated by measuring their activity in Established Experimental Allergic Encephalomyelitis (EEAE) as follows:

Testing is carried out analogously to that described above with the exception that the administration of the test compound commences on day 8 to day 9 after sensitization (i.e., immediately prior to appearance of disease symptoms) at dosages of from 5 to 50 mg/kg/day either daily or every second day and continuing for 2 weeks. During the testing period, the animals are examined daily for symptoms of the disease and scored as in the above test method.

On administration of SDZ 62-826 and SDZ 62-834 at the above dosage rates, a substantial reduction of appearance of EAE disease symptoms is observed over the test period in comparison with appearance in control groups receiving placebo.

The precise dosage of a compound of formula I, or a corresponding hydrate, II, III, IV or V to be employed in treating multiple sclerosis depends upon several factors including the host, the nature and the severity of the condition being treated, the mode of administration and the particular compound employed. However, in general, satisfactory inhibition of the symptoms of multiple sclerosis is achieved when a compound of formula I, II, III, IV or V is administered orally at a daily dosage of 0.5-30 mg/kg body weight, preferably 1-20 mg/kg or, for most larger primates, at a total daily dosage of 35-600 mg. A preferred total daily dosage for most larger primates is 150 to 300 mg.

Usually, a small dosage is administered initially and the dosage is gradually increased until the optimal dosage for the host under treatment is determined. The upper limit of dosage is that imposed by side effects, and can be determined by trial for the host being treated, including humans.

As indicated above, a preferred total daily dosage for most larger primates, e.g., humans, is 150 to 300 mg. However, it should be understood that when a clear improvement in the symptoms of multiple sclerosis is observed upon daily administration of between 150 and 300 mg of a compound of formula I, II, III, IV or V, the dosage regimen can be decreased to between 150 and 300 mg of a compound of formula I, II, III,, IV or V every second day.

The compounds of formulae I, and the corresponding hydrates, II, III, IV and V may be combined with one or more pharmaceutically acceptable carriers and, optionally, one or more conventional pharmaceutical adjuvants and administered orally in the form of tablets, dispersible powders, granules, capsules, elixirs, suspensions and the like. The compositions may be prepared by conventional means.

The compounds of formulae I, II, III, IV and V may be formulated into such pharmaceutical compositions containing an amount of the active substance that is effective in treating multiple sclerosis, such compositions in unit dosage form and such compositions comprising a solid pharmaceutically acceptable carrier.

Tablets and capsules containing the ingredients indicated below may be prepared by conventional techniques and are useful in treating multiple sclerosis when administered once a day.

| Ingredients | Weight (mg) tablet | capsule |
|---|---|---|
| compound of formula III, e.g., SDZ 62-834 | 150 | 150 |
| tragacanth | 10 | — |
| lactose (spray-dried) | 197.5 | 250 |
| corn starch | 25 | — |
| talcum | 15 | — |
| magnesium stearate | 2.5 | — |
| Total | 400.0 | 400 |

The preferred pharmaceutical compositions from the standpoint of preparation and ease of administration are solid compositions, particularly liquid or hard-filled capsules and tablets containing from about 150-300 milligrams of the active ingredient.

What is claimed is:

1. A method of treating multiple sclerosis comprising administering to a subject afflicted therewith a therapeutically effective amount of a compound of formula I:

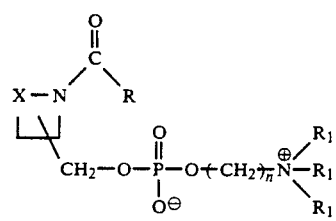

where

R is n-$C_{14}$-$C_{20}$alkyl or O-n-$C_{14}$-$C_{20}$alkyl;

each $R_{1'}$ independently, is methyl or ethyl;

n is an integer 2 to 6; and

X is $-(CH_2)_m-$, where m is 2 to 4; $CH_2CH_2O$ or $CH_2CH_2S$, with the proviso that when X is $CH_2CH_2O$ or $CH_2CH_2S$, the nitrogen atom is attached to the $\beta$-carbon atom of said groups;

or a corresponding hydrate thereof.

2. A method according to claim 1 comprising administering a therapeutically effective amount of a compound of formula Ia:

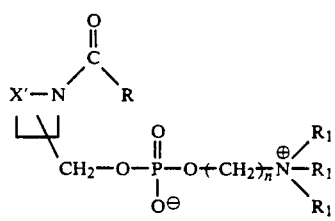

where

X is $-(CH_2)_{2-4}-$ and R, each $R_1$ and n are as defined in claim 1;

or a corresponding hydrate thereof.

3. A method according to claim 2 comprising administering a therapeutically effective amount of a compound of formula Ia':

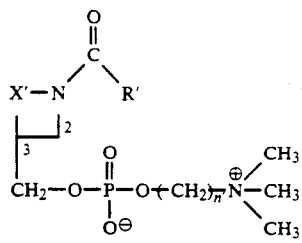

where
R' is n-$C_{14}$-$C_{18}$alkyl or O-n-$C_{14}$-$C_{18}$alkyl;
n' is an integer 2 to 4; and
X' is as defined in claim 2;
or a corresponding hydrate thereof.

4. A method according to claim 3 comprising administering a therapeutically effective amount of a compound having the formula

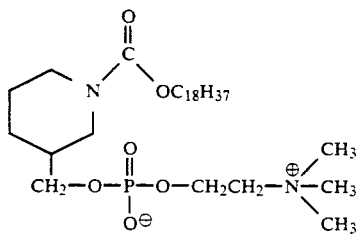

5. A method according to claim 3 comprising administering a therapeutically effective amount of a compound having the formula

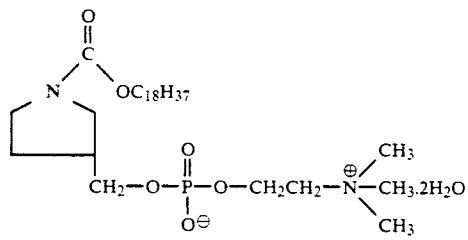

6. A method according to claim 3 comprising administering a therapeutically effective amount of a compound having the formula

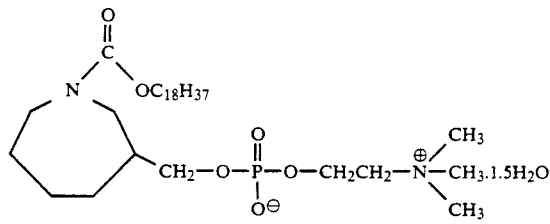

7. A method according to claim 1 comprising administering a therapeutically effective amount of a compound of formula Ib:

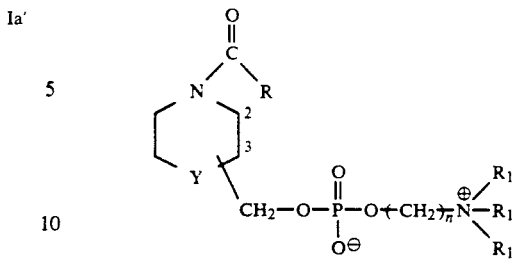

where
Y is —O— or —S—, and R,
each $R_1$ and n are as defined in claim 1;
or a corresponding hydrate thereof.

8. A method according to claim 7 comprising administering a therapeutically effective amount of a compound of formula Ib':

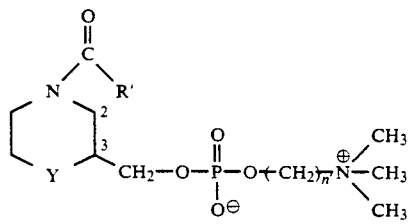

where
R' is n-$C_{14}$-$C_{18}$alkyl or O-n-$C_{14}$-$C_{18}$alkyl;
n' is an integer 2 to 4; and
Y is as defined in claim 7;
or a corresponding hydrate thereof.

9. A method according to claim 8 comprising administering a therapeutically effective amount of a compound having the formula

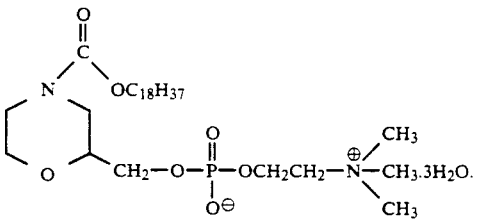

10. A method according to claim 8 comprising administering a therapeutically effective amount of a compound having the formula

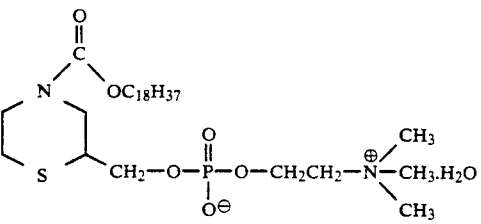

* * * * *